(12) United States Patent
Malinin

(10) Patent No.: US 10,549,011 B2
(45) Date of Patent: Feb. 4, 2020

(54) BONE PUTTY AND GEL SYSTEMS AND METHODS

(71) Applicant: Theodore Malinin, Key Biscayne, FL (US)

(72) Inventor: Theodore Malinin, Key Biscayne, FL (US)

(73) Assignee: Osteolife Biomedical, LLC, Miami, FL (US)

( * ) Notice: Subject to any disclaimer, the term of this patent is extended or adjusted under 35 U.S.C. 154(b) by 0 days.

(21) Appl. No.: 14/923,057

(22) Filed: Oct. 26, 2015

(65) Prior Publication Data

US 2017/0112963 A1   Apr. 27, 2017

(51) Int. Cl.
*A61L 27/36* (2006.01)
*A61L 27/24* (2006.01)

(52) U.S. Cl.
CPC ............ *A61L 27/365* (2013.01); *A61L 27/24* (2013.01); *A61L 27/3608* (2013.01); *A61L 27/3691* (2013.01); *A61L 2300/30* (2013.01); *A61L 2400/06* (2013.01); *A61L 2430/02* (2013.01)

(58) Field of Classification Search
CPC .... A61L 27/365; A61L 27/3608; A61L 27/24; A61L 27/3691; A61L 2430/02; A61L 2400/06; A61L 2300/30
See application file for complete search history.

(56) References Cited

U.S. PATENT DOCUMENTS

| | | |
|---|---|---|
| 4,172,128 A | 10/1979 | Thiele et al. |
| 4,191,747 A | 3/1980 | Scheicher |
| 4,277,238 A | 7/1981 | Katagirl |
| 4,394,370 A | 7/1983 | Jefferies |
| 4,725,234 A | 2/1988 | Ethridge |
| 4,743,259 A | 5/1988 | Bolander et al. |
| 4,851,046 A | 7/1989 | Low et al. |
| 4,904,261 A | 2/1990 | Dove |
| 4,932,973 A | 6/1990 | Gendler |
| 5,053,049 A | 10/1991 | Campbell |
| 5,073,373 A | 12/1991 | O'Leary et al. |
| 5,112,354 A | 5/1992 | Sires |
| 5,290,558 A | 3/1994 | O'Leary et al. |
| 5,306,304 A | 4/1994 | Gendler |
| 5,458,638 A | 10/1995 | Kuslich |
| 5,464,439 A | 11/1995 | Gendler |
| 5,507,813 A | 4/1996 | Dowd |
| 5,516,532 A | 5/1996 | Atala et al. |
| 5,556,430 A | 9/1996 | Gendler |
| 5,756,145 A | 5/1998 | Darouiche |
| 5,860,973 A | 1/1999 | Michelson |
| 5,866,155 A | 2/1999 | Laurencin et al. |
| 6,030,635 A | 2/2000 | Gertzman et al. |
| 6,224,630 B1 | 5/2001 | Bao |
| 6,241,771 B1 | 6/2001 | Gresser |
| 6,245,108 B1 | 6/2001 | Biscup |
| 6,277,149 B1 | 8/2001 | Boyle |
| 6,293,970 B1 | 9/2001 | Wolfinbarger, Jr. et al. |
| 6,325,806 B1 | 12/2001 | Fox |
| 6,530,955 B2 | 3/2003 | Boyle |
| 6,576,249 B1 | 6/2003 | Gendler et al. |
| 6,591,581 B2 | 7/2003 | Schmieding |
| 6,632,247 B2 | 10/2003 | Boyer, II |
| 6,660,038 B2 | 12/2003 | Boyer, II |
| 6,843,807 B1 | 1/2005 | Boyce et al. |
| 6,855,169 B2 | 2/2005 | Boyer, II et al. |
| 6,887,272 B2 | 5/2005 | Shinomiya |
| 6,936,816 B2 | 8/2005 | Mankos et al. |
| 6,942,698 B1 | 9/2005 | Jackson |
| 6,986,788 B2 | 1/2006 | Paul |
| 7,018,412 B2 | 3/2006 | Ferreira |
| 7,077,866 B2 | 7/2006 | Gresser |
| 7,115,146 B2 | 10/2006 | Boyer |
| 7,335,381 B2 | 2/2008 | Malinin et al. |
| 7,473,277 B2 | 1/2009 | Boyer, II |
| 7,838,040 B2 | 11/2010 | Malinin |
| 7,879,103 B2 | 2/2011 | Gertzman et al. |

(Continued)

FOREIGN PATENT DOCUMENTS

CN   1861197   11/2006

OTHER PUBLICATIONS

Malinin, T., Acquisition and Banking of Bone Allografts, Bone Grafts & Bone Substitutes, Edited by M.B. Hebei and Reddi. Philadelphia, WB Saunders Company, Aug. 17, 1992, pp. 206-225.
Malinin, T. & Temple, H. T., Musculoskeletal Tissue Transplantation and Tissue Banking, Jaypee Brothers Medical (P) Ltd., New Delhi, India, Aug. 28, 2013.
Malinin et al., "Particulate Bone Allograft Incorporation in Regeneration of Osseous Defects, Importance of Particle Sizes", The Open Orthopaedics Journal, 2007, vol. 1, pp. 19-24.

(Continued)

*Primary Examiner* — Lezah Roberts
(74) *Attorney, Agent, or Firm* — Akerman LLP

(57) ABSTRACT

A collagen-bone composition may include bone collagen and bone particles. The collagen may be in the form of a collagen suspension and the bone particles may be demineralized bone particles retained in collagen suspension. The composition may be prepared from pressure and thermal treatment of dry demineralized bone particles contacted with an aqueous medium to produce a viscous gel-like fluid. The fluid may include the collagen extracted from the demineralized bone particles. Addition of particulate bone may be used to increase the consistency of the composition, which may convert it into a paste or putty. The paste or putty may be suitable for ejection from a syringe. The collagen-bone composition may be preserved by freeze-drying or preferably by hypothermic dehydration. On reconstitution with aqueous medium, the preserved material may resume its original shape and properties.

21 Claims, 6 Drawing Sheets

(56) References Cited

U.S. PATENT DOCUMENTS

| | | |
|---|---|---|
| 8,182,532 B2 | 5/2012 | Anderson |
| 8,202,539 B2 | 6/2012 | Behnam et al. |
| 8,268,008 B2 | 9/2012 | Betz et al. |
| 8,298,566 B2 * | 10/2012 | Markoulides ....... A61L 27/3608 106/124.7 |
| 8,318,212 B2 | 11/2012 | Malinin |
| 8,337,780 B2 | 12/2012 | Gaskins et al. |
| 8,357,384 B2 | 1/2013 | Behnam et al. |
| 8,403,986 B2 | 3/2013 | Michelson |
| 8,574,825 B2 | 11/2013 | Shelby et al. |
| 8,608,801 B2 | 12/2013 | Hung et al. |
| 8,608,803 B2 | 12/2013 | Sybert |
| 8,709,087 B2 | 4/2014 | Cragg |
| 8,791,071 B1 | 7/2014 | Malinin |
| 8,888,823 B1 | 11/2014 | Malinin |
| 8,936,816 B1 | 1/2015 | Anderson et al. |
| 8,940,692 B2 | 1/2015 | Malinin |
| 8,940,698 B2 | 1/2015 | Malinin |
| 9,101,424 B1 | 8/2015 | Malinin et al. |
| 9,611,043 B2 | 4/2017 | Malinin et al. |
| 9,839,524 B2 | 12/2017 | Malinin et al. |
| 2001/0008980 A1 | 7/2001 | Gresser |
| 2001/0034553 A1 | 10/2001 | Michelson |
| 2003/0143256 A1 | 7/2003 | Gen |
| 2004/0068234 A1 | 4/2004 | Martin et al. |
| 2004/0107003 A1 | 6/2004 | Boyer, II |
| 2004/0169311 A1 | 9/2004 | Bonutti |
| 2005/0008672 A1 * | 1/2005 | Winterbottom ......... A61L 27/40 424/423 |
| 2005/0196460 A1 | 9/2005 | Malinin |
| 2005/0244457 A1 | 11/2005 | Reddi |
| 2006/0074466 A1 | 4/2006 | Malinin |
| 2006/0206208 A1 | 9/2006 | Michelson |
| 2006/0279625 A1 | 12/2006 | Malinin |
| 2007/0098756 A1 | 5/2007 | Behnam |
| 2007/0191963 A1 | 8/2007 | Winterbottom et al. |
| 2007/0231788 A1 | 10/2007 | Behnam et al. |
| 2008/0091270 A1 | 4/2008 | Miller |
| 2008/0234822 A1 | 9/2008 | Govil |
| 2008/0279825 A1 | 11/2008 | Malinin |
| 2009/0017095 A1 | 1/2009 | Barnouin et al. |
| 2009/0018659 A1 | 1/2009 | Malinin |
| 2009/0155378 A1 | 6/2009 | Behnam et al. |
| 2009/0269388 A1 | 10/2009 | Sunwoo et al. |
| 2009/0312842 A1 | 12/2009 | Bursac et al. |
| 2009/0318934 A1 | 12/2009 | Johnson et al. |
| 2010/0268339 A1 | 10/2010 | Malinin |
| 2010/0274362 A1 | 10/2010 | Yayon et al. |
| 2010/0310623 A1 | 12/2010 | Laurencin et al. |
| 2011/0009967 A1 | 1/2011 | Malinin |
| 2011/0071536 A1 | 3/2011 | Kleiner et al. |
| 2011/0104242 A1 | 5/2011 | Malinin |
| 2011/0118850 A1 | 5/2011 | Govil et al. |
| 2011/0208190 A1 | 8/2011 | Kumbar et al. |
| 2011/0208305 A1 | 8/2011 | Malinin et al. |
| 2012/0121660 A1 * | 5/2012 | Akella ................ A61L 24/0063 424/400 |
| 2012/0195971 A1 | 8/2012 | Missos et al. |
| 2012/0245703 A1 | 9/2012 | Meredith |
| 2013/0079889 A1 | 3/2013 | Spillman |
| 2013/0108595 A1 | 5/2013 | Gimble et al. |
| 2013/0184835 A1 | 7/2013 | Ferrari et al. |
| 2013/0209956 A1 | 8/2013 | Sanders |
| 2013/0316012 A1 | 11/2013 | Gaskins et al. |
| 2013/0338792 A1 | 12/2013 | Schmieding et al. |
| 2014/0005793 A1 | 1/2014 | Koford et al. |
| 2014/0065239 A9 | 3/2014 | Behnam et al. |
| 2014/0134212 A1 | 5/2014 | Shi et al. |
| 2014/0255506 A1 | 9/2014 | Behnam et al. |
| 2015/0012107 A1 | 1/2015 | Koford et al. |
| 2015/0140096 A1 | 5/2015 | Malinin |
| 2015/0028243 A1 | 9/2015 | Malinin |
| 2015/0258243 A1 | 9/2015 | Malinin |
| 2017/0128633 A1 | 5/2017 | Malinin |
| 2017/0128634 A1 | 5/2017 | Malinin |
| 2017/0202645 A1 | 7/2017 | Malinin |
| 2017/0266355 A1 | 9/2017 | Malinin |

OTHER PUBLICATIONS

Povidone-Iodine Prevents Infection in Prosthetic Implants, Outpatient Surgery, Mar. 7, 2011, accessed online at http://www.outpatientsurgery.net/newsletter/eweekly/2011/03/08/povidone-iodine-prevents-infection-in-prosthetic-implants.
International Search Report issued in connection with PCT/US2015/036384.
Written Opinion of the International Searching Authority issued in connection with PCT/US2015/036384.
Osteosponge, Bacterin, www.bacterin.com.
International Search Report issued in PCT/US2015/014618.
Written Opinion of the International Search Authority issued in PCT/US2015/014618.
U.S. Appl. No. 16/148,289, filed Oct. 1, 2018.
U.S. Appl. No. 15/477,778, filed Apr. 3, 2017.
U.S. Appl. No. 15/611,038, filed Jun. 1, 2017.

* cited by examiner

BONE PUTTY AND GEL SYSTEMS AND METHODS

TECHNICAL FIELD

The present disclosure relates to compositions and methods of delivery of bone particles. More specifically, the present disclosure relates to collagen-demineralized bone compositions and methods of delivery of bone particles, particularly collagen-demineralized bone compositions having bone particles retained or suspended in bone collagen extracted from the bone particles.

BACKGROUND

Malleable bone compositions to deliver demineralized bone particles to osseous defects and effect spinal fusion include carrier based technologies. Conventional carrier based bone particle compositions have employed a patient's own blood as a vehicle in which both demineralized and non-demineralized bone particles are suspended.

Various alternatives to use of blood as a carrier have also been proposed. A composition termed Grafton, described in U.S. Pat. No. 5,073,373, a registered trademark of Osteotech, Inc., is a mixture of demineralized bone particles 1000 microns to 12,000 microns in size. Grafton purports to allow the surgeon to conveniently place allograft bone at the surgical site.

A bone gel and putty produced by dissolving demineralized bone matrix in an aqueous solution at temperatures above 25° C. is described in U.S. Pat. No. 6,576,249. The resulting viscous supernatant is cooled and mixed with non-demineralized or demineralized bone particles to produce a gel or putty-like material. A flowable demineralized bone powder composition with large particle sizes between 0.1 cm to 1.2 cm suspended in a low molecular weight polyhydroxy compound is described in U.S. Pat. No. 5,290,558. Another bone composition including demineralized bone material mixed with a carrier for reconstructing bone or tooth defects is described in U.S. Pat. No. 4,172,128. The carrier is made by adding a mucopolysaccharide to mineralized bone colloidal material. The composition is prepared by dissolving bone or tooth tissue in a solvent forming a colloidal solution. To this is added inert polyhydroxy compounds such as polyuronic acid. Hydrogen or polyvalent metal ions are added to from a gel. The gel is purported to be flowable at temperatures above 35° C. Still another method for making bone putty or gel is described in U.S. Pat. No. 6,030,635. Bone powder is suspended in a carrier consisting of sodium hyaluronate, chitosan, and N, O-carboxymethylchitosan in an aqueous solution. An additional hydrogel is also described. Another bone particle composition including bone meal is described in U.S. Pat. No. 4,191,747 wherein it is advocated that osseous defects be filled with coarsely ground, denatured bone meal freed from fat. The bone meal is mixed with polysaccharide in saline solution and applied to a bone defect.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

SUMMARY

Figure 1:
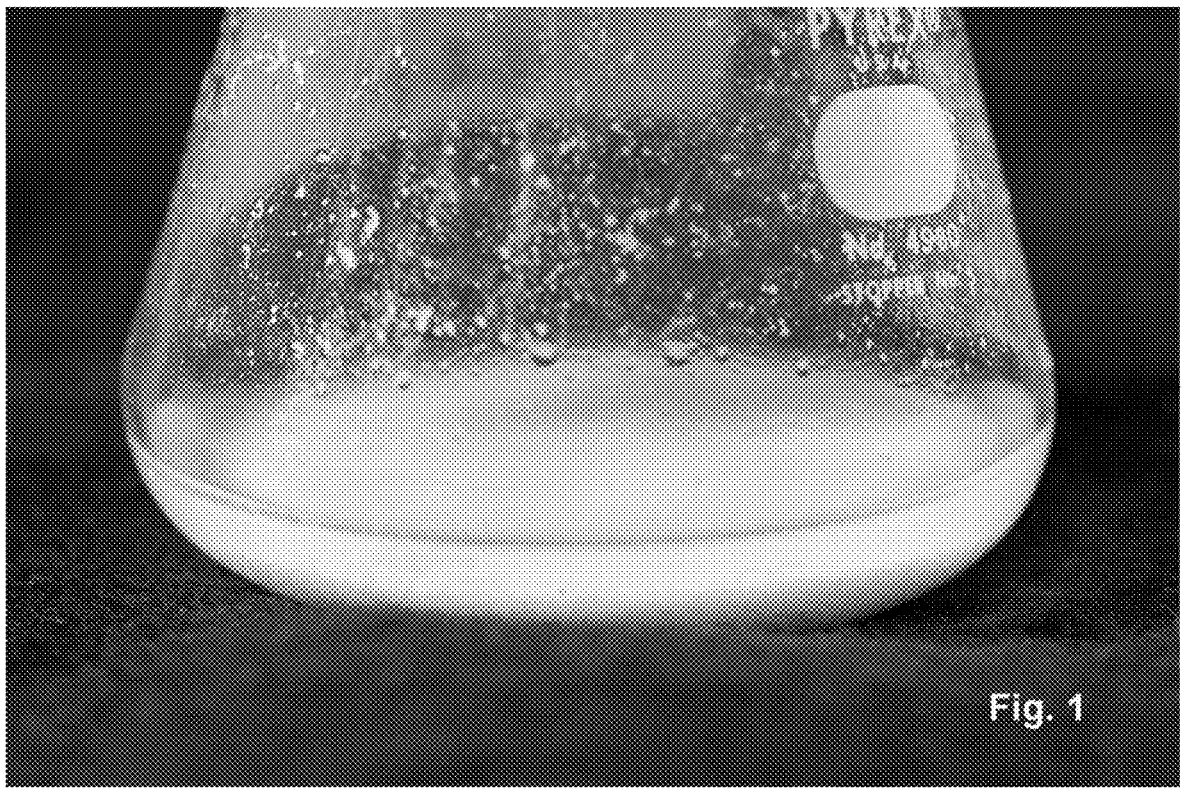
FIG. 1 is a photograph of an extraction mixture wherein bone particles (bottom of flask) have been extracted by pressure of approximately 15 psi and temperature of approximately 120° C. according to various embodiments described herein. The supernatant fluid contains the viscous bone collagen. The bone particles and collagen may be mixed by agitation.

In one aspect, a bone particle composition in a carrier may comprise a plurality of bone particles and a carrier. The bone particles may comprise demineralized or partially demineralized bone particles or both. The carrier may comprise bone collagen extracted from the bone particles, wherein the bone particles are retained or suspended in the carrier. The bone composition may be freeze-dried, hypothermically dehydrated, chemical dehydrated, or desiccated. The bone particles may be between approximately 10 microns and approximately 900 microns. The bone particles may comprise bone fluff with particle sizes ranging from approximately 100 microns to approximately 3000 microns in length and approximately 40 microns to approximately 60 microns in width.

In various embodiments, the bone particle composition may be between approximately 3% to approximately 50% by weight bone. The bone particles may be from a single donor. The weight ratio of collagen to bone particles in the composition may be between approximately 6:10 to approximately 7:10. In one embodiment, the bone particles comprise bone selected from the group consisting of allogeneic bone, xenogeneic bone, and combinations thereof. In one example, the bone particles comprise AAA bone.

In another aspect, a method of making a collagen-bone mixture may comprise contacting bone particles with an aqueous medium, wherein the bone particles comprise dried bone that has been demineralized, partially demineralized, or a combination thereof. The method may further comprise extracting bone collagen from the bone particles to form an extraction mixture of the bone particles and bone collagen. The extracting may comprise exposing the bone particles contacted with the aqueous medium to an elevated temperature and high pressure treatment sufficient to extract the bone collagen from the bone particles. The method may further comprise cooling the mixture of bone particles and bone collagen.

In various embodiments, the pressure treatment may be provided by steam pressure. The bone particles may comprise bone materials selected from the group consisting of allogeneic bone, xenogeneic bone, and combinations thereof. The bone particles may be between approximately 10 microns and approximately 900 microns. In one example, the bone particles comprise bone fluff with particle sizes ranging from approximately 100 microns to approximately 3000 microns in length and approximately 40 microns to approximately 60 microns in width. The aqueous medium may comprise blood serum, water, saline, balanced salt solution, or combination thereof.

In various embodiments, the aqueous medium may contact the bone particles at temperatures greater than 36° C. In one embodiment, the aqueous medium may contact the bone particles at temperatures between approximately 60° C. and approximately 120° C. The aqueous medium and bone particles may be maintained at an average temperature of approximately 120° C. or greater during the pressure treatment. The pressure treatment may comprise exposing the bone particles contacted with the aqueous medium to a pressure of at least 15 psi. In one embodiment, the pressure treatment may be carried out for less than 60 minutes. In one embodiment, the pressure treatment may be carried out for 30 minutes or longer. The mixture of bone particles contacted with the aqueous medium may comprises between approximately 20% to approximately 60% aqueous medium by volume and the elevated temperature and high pressure treatment may be applied to the mixture to achieve an extraction mixture viscosity of above approximately 2 centipoise. The bone particles may be substantially intact in the extraction mixture.

In some embodiments, the method may further comprise modifying the consistency of the extraction mixture of bone particles and bone collagen to form a gel, paste, or putty. Modifying the consistency of the mixture after extraction may comprise addition of additional bone particles. Modifying the consistency of the mixture after extraction may comprise condensing the mixture. Modifying the consistency of the mixture after extraction may comprise concentrating the mixture by evaporation. The modified consistency extraction mixture may comprise between approximately 3% to approximately 50% by weight bone. The bone particles may be from a single donor. The weight ratio of collagen to bone particles may be between approximately 6:10 to approximately 7:10, for example.

The method may further comprise preserving the extraction mixture or modified consistency extraction mixture. Preserving the extraction mixture may include freeze-drying, hypothermic dehydration, chemical dehydration, or desiccation. The method may further comprise reconstituting the preserved extraction mixture with an amount aqueous medium to form a reconstituted extraction mixture having a gel, paste, or putty consistency. The aqueous medium may comprise water, salt solution, or a combination thereof. The salt solution may comprise saline, phosphate buffered saline, lactated Ringer's solution, balanced salt solution, or a combination thereof. Reconstituting may comprise controlling the amount of aqueous medium in the reconstituted extraction mixture. Reconstituting may further comprise addition of additional bone particles, condensation of collagen by evaporation, or a combination thereof. The reconstituted extraction mixture may comprises between approximately 3% to approximately 50% by weight bone.

DESCRIPTION

Conventional carrier based bone particle compositions have employed a patient's own blood as a vehicle in which both demineralized and non-demineralized bone particles are suspended. A difficulty when using blood as a carrier of allograft bone particles is the inconvenience of mixing the same with bone particles at the operative site and producing a composition of desired consistency even if blood is anticoagulated. For example, blood contains about 40% to 50% of red blood cell mass, which produces a hematoma. Because the hematoma is not resorbed for several weeks it can serve as a site for harboring infection.

Various alternatives to use of blood as a carrier, such as Grafton, described in U.S. Pat. No. 5,073,373, a registered trademark of Osteotech, Inc., purports to allow the surgeon to conveniently place allograft bone at the surgical site. A difficulty with Grafton, however, is lack of retention at the site of application. This may be because Grafton employs glycerol, which has a low molecular weight (92.09 g/mol) and high water solubility. Thus, glycerol easily dissolves in blood. The viscosity of glycerol is also reduced when its temperature is raised from ambient (room temperature) to the temperature of the body (37° C.). The low viscosity and water solubility of glycerol may cause the bone particles to flow away from the site when GRAFTON had been placed. Some compositions that depend on synthetic components may set up an immunologic response in a human recipient. Other bone particle compositions have included demineralized bone particles, either human or bovine, from various sources in collagen. Collagen prepared form various sources, absorbs slowly in human body, which can delay the formation of new bone, and produce scar formation instead. Other compositions that rely on complete removal of fat might be a disadvantage as certain amount of intraosseous lipid is required to transport bone morphogenetic proteins (BMPs).

Collagen-bone preparations and methods of making collagen-bone preparations comprising bone collagen and bone particles retained therein, wherein the source of the bone collagen comprises the retained bone, are described herein. The collagen-bone preparations may find use, for example, treating bone lesions or defects, such as filling recesses in bone defects.

The collagen-bone preparations may comprise demineralized or partially demineralized bone and bone collagen matrix extracted from the same. As used herein, demineralized includes decalcified. The demineralized or partially demineralized bone may be suspended in the extracted bone collagen. The demineralized or partially demineralized bone may be suspended in the bone collagen within an aqueous medium. The aqueous medium may comprise a water solution, salt solution, or other biologically suitable medium, e.g., an aqueous medium having components or characteristics similar to blood serum. The collagen-bone preparation may be prepared from an extraction mixture comprising the demineralized or partially demineralized bone and the bone collagen extracted from the demineralized or partially demineralized bone. The extraction mixture may be obtained by application of steam pressure and high temperature to the demineralized or partially demineralized bone particles until the viscous bone collagen is extracted while the bone particles remain intact. Prior to extraction, the demineralized or partially demineralized bone may be dried and particulated. In one embodiment, the dry bone particles are microstranded and have an appearance resembling cotton wood. The extraction may include contacting the dry demineralized or partially demineralized bone particles with aqueous medium wherein the bone particles are contacted or mixed with the aqueous medium during the application of steam pressure and high temperature. A desired consistency, such as gel, paste, or putty, may be achieved by modifying the amount of aqueous medium added to the dry demineralized or partially demineralized bone particles.

The extraction mixture comprising the viscous bone collagen matrix, demineralized bone, and aqueous medium may be formulated to have a flowable consistency. For example, the extraction material may be prepared to comprise a viscous gel-like fluid, which may be converted into a collagen-bone preparation having the consistency of a gel, paste, or putty. The amount of aqueous medium contacted with the particles during the extraction process may impact viscosity of the collagen-bone extraction mixture. The collagen-bone preparation may further comprise additional bone particles added to the collagen-bone extraction mixture to achieve a desired gel, paste, or putty consistency and to increase its osteogenic potential. The collagen-bone preparation at the desired consistency may be used for surgical transplantation in the treatment of bone lesions. For example, the gel, paste, or putty may be formulated to have a flowable consistency that may be utilized in delivery of the preparation to the application site. In one embodiment, the consistency may be that of a flowable gel, paste, or putty that may be expressed from a syringe. In addition to the consistency, the dimensions of the bone particles may be modified to suit a desired delivery device. For example, the bone particles may be sized such that they may be delivered to the application site through a bevel of a syringe.

Following extraction of the bone collagen, the collagen-bone preparation or extraction mixture may be preserved by drying. The dried collagen-bone preparation or extraction mixture may be subsequently reconstituted to assume the characteristics of the original mixture or to achieve a desired consistency. Reconstitution may be with an aqueous medium, such as water or various salt solutions, as described herein. A desired consistency, such as gel, paste, or putty, may be achieved by modifying the amount of aqueous medium added to the dried collagen-bone preparation. Additionally or alternatively, a desired consistency, such as gel, paste, or putty, may be achieved by addition of bone particles, such as non-demineralized, demineralized, or partially demineralized bone particles, to the collagen-bone preparation prior to, during, or after reconstitution.

A method of making the collagen-bone preparation wherein the bone particles are retained in a bone collagen matrix carrier extracted from the bone particles may comprise extracting bone matrix collagen from dried demineralized or partially demineralized bone particles prepared from donor bone. The flowable carrier bone collagen may be extracted from demineralized donor bone. Unless specified otherwise, demineralized may include demineralized as well as partially demineralized. The donor bone may be an allogeneic source or, in some embodiments, an xenogeneic source. The preparation may be prepared from a single source. The preparation may be further prepared from a single source from a single donor. The bone may typically comprise cortical bone. Demineralization may be performed according to methods known in the art. In one embodiment, the bone is demineralized by contacting, such as submerging, the bone in a decalcifying solution. The decalcifying solution may be HCl, citric acid, or other suitable decalcifying solution.

The bone may be dried following demineralization treatment. For example, the demineralized or partially demineralized bone may be freeze-dried (lyophilized) or hypothermically dehydrated. Drying, such as by freeze-drying or hypothermic dehydration, alters the physical make-up of bone matrix allowing for the release or extraction of bone collagen material according to the methods disclosed herein. In contrast, non-demineralized bone has not been found to yield a comparable result.

Prior to or after the bone is demineralized, dried, or both, the bone may be particulated. The bone particles may comprise various configurations of dimensions and sizes. In one embodiment, the bone is particulated to comprise particle sizes adapted for delivery with a delivery device. For example, bone particles may comprise dimensions between approximately 10 and approximately 900 microns adapted for delivery from a conventional syringe. The particulate bone may be prepared to comprise shapes configured to provide beneficial biomechanical properties. The particulate bone may also be prepared to comprise shapes configured to assist or accelerate extraction of bone collagen. The shapes may include high surface area shapes compared to conventional bone particles. In some embodiments, however, the particles may not comprise high surface area shapes. Example shapes include shavings, parings, powder, granules, grated material, fillings, and scrapings. Particles having high surface area may provide greater access to steam pressure for extraction of bone collagen. The high surface area particles, may comprise a thickness and width significantly less than its length. The length, for example, may be orders of magnitude greater than the thickness or width. In some such embodiments, the particles comprise fine microstrands. In one such embodiment, a bone particle preparation may comprise a mixture of delicate high surface area bone particles, which may be referred to herein as bone fluff. The bone fluff may resemble cottonwood and comprise a plurality of branching, interwoven bone microstrands. In one embodiment, the bone particles may vary in size from about 10 microns to approximately 3000 microns in length, approximately 40 microns to approximately 60 microns in width, and approximately 10 microns to approximately 100 microns in thickness. In one such embodiment, the particle size may allow suitable passage of the implant material through a bevel of a conventional, commercially available syringe. However, larger bone particles may also be used, e.g., for implantation procedures or implantation devices in which the larger bone particles are suitable. In one embodiment, bone particles may comprise a dimension between approximately 1 cm to approximately 1.5 cm.

In another embodiment, the donor bone in which the matrix gel or putty comprising bone particles suspending in collagen is extracted comprises chemo sterilized, autolyzed antigen extracted (AAA) bone of Urist. The bone may be allogeneic bone or xenogeneic bone. Various embodiments of the present methods may be employed to minimize antigenicity of the preparation compared to current treatment processes. In one embodiment, auto digestion of the bone in neutral buffer solutions may be employed to removes soluble proteins from the bone that are capable of producing alloimmune response. In these or other embodiments, exposure of the bone after chloroform-methanol extraction to 0.6N HCl at 2° C. may be employed to surface demineralize bone surfaces, making it suitable for extraction according to the extraction methods disclosed herein. In these or other embodiments, treatment of the bone with 10 mg/liter iodoacetic acid and 10 mg/liter of sodium azide may be used to perform endogenous intracellular and extracellular enzymatic autodigestion of transplantation antigens with preservation of bone morphogenetic proteins (BMPs) by sulfhydryl group enzyme inhibitors. (Marshall R. Urist. Bone transplantation. In: *Fundamental and clinical and bone physiology*. (M. R. Urist ed.) J. B. Lippincoll Company, Philadelphia. Toronto 1980 pp. 348-355). An advantage of this embodiment is that AAA bone is rich in BMPs. The process of repair with AAA bone is believed to depend upon retention of BMPs and be enhanced by the extraction of undesirable soluble tissue antigens from bone. In some applications, AAA bone as the donor bone source may be more rapidly resorbed and replaced than many bone allografts prepared by other methods.

Extraction of the bone collagen may include subjecting the bone particles to pressure treatment comprising, for example, a steam pressure treatment. The extraction may also include subjecting the demineralized bone particles to a temperature treatment comprising elevated temperatures. Current methods to extract collagenous bone matrix include dissolving the bone and separating the extracted collagenous bone matrix. However, as disclosed herein, collagenous material may be removed from the particulate bone while retaining the basic framework of the bone. Unlike previous methods to extract collagen that rely on separating the collagen gel mixture from the bone from which it had been extracted, and which is dissolved in the process, the present extraction process may be performed to remove collagenous material, effectively only collagenous material, or otherwise without dissolving the bone, thus, retaining the basic framework of bone. Additionally, the present extraction process may be performed without the damaging agitation and sonication of previous methods.

According to various embodiments, the dried demineralized particulate bone is the source of the collagenous material, which may be extracted from the dry demineralized or partially demineralized particulate bone following contact with the aqueous medium and upon application of pressure and temperature treatment. Extraction of bone matrix collagen from the dry demineralized or partially demineralized bone particles may be performed in an aqueous medium, which may be an aqueous solution. The aqueous medium may be contacted with the dry bone particles at an elevated temperature or may be heated prior to, during application of the high pressure treatment, or both. The resulting extraction mixture may comprise a flowable mixture of particulate bone suspended in extracted collagen matrix. The extraction mixture may be cooled whereby the mixture takes on a gelatinous consistency.

The aqueous medium contacted with the dry demineralized or partially demineralized bone particles may comprise distilled water, for example. The extraction may also be performed with other biologically compatible aqueous mediums, such as solutions comparable in composition to blood serum, such as an aqueous salt solution. In one embodiment, the aqueous medium comprises an isotonic solution. The isotonic solution may comprise an aqueous saline solution, e.g., a sodium chloride 0.9% solution. In contrast to current methods that require damaging agitation or sonication for collagen extraction, such steps are not required according to the methods disclosed herein. Rather the extraction of collagenous bone matrix may be achieved by subjecting the mixture of demineralized bone in aqueous solution to pressure treatment. The pressure treatment may also comprise thermal temperature treatment. For example, extraction of viscous collagen matrix from the bone particles may be achieved by subjecting the mixture to steam under pressure at an elevated temperature.

In an embodiment of such a method, the steam pressure is preferably from approximately 15 psi to approximately 30 psi and the elevated temperature is preferably in the range of 100° C.±20, depending on the elevation. For example, lower temperature ranges may be applicable at higher elevations relative to steam pressure. Under typical extraction conditions, the process may take from between approximately 15 minutes to approximately 60 minutes. The time of the exposure of the bone particles to steam pressure should be closely monitored and determined. Too long an exposure may result in undesirable dissolution of the bone. Too little exposure may result in insufficient extraction of bone collagen. In one embodiment of the method, the time of exposure is determined by observation of the bone particles such that the pressure and thermal treatment is terminated when the supernatant fluid is thick and viscous. The pressure and thermal treatment is preferably terminated when the supernatant fluid is thick and viscous and the bone particles are substantially intact. In one embodiment, for example, the pressure and thermal treatment is applied until the extraction mixture has a viscosity above approximately 2 centipoise, but before significant bone dissolution occurs. The viscosity may vary depending on the amount of aqueous medium in the mixture of bone particles and aqueous medium. In one embodiment, the amount of aqueous medium or liquid added to the bone particles is between approximately 20% to approximately 60% by volume. In one embodiment, the amount of aqueous medium in the mixture of bone particles and aqueous medium comprises between approximately 20% to approximately 60% aqueous medium by volume, and the elevated temperature and high pressure treatment is applied to achieve an extraction mixture viscosity of above approximately 2 centipoise. The aqueous medium may contact the bone particles at a temperature greater than 36° C. For example, the aqueous medium may contact the bone particles at a temperature between approximately 60° C. and approximately 120° C. The elevated temperature thermal treatment and high pressure treatment may include applying an average temperature approximately 120° C. or greater and a pressure of at least 15 psi during the extraction. As introduced above, the extraction may be performed to substantially extract the collagen without dissolution of the bone particles to obtain a viscous extraction mixture. In one embodiment, the elevated temperature and high pressure are applied for 30 minutes or longer, such as between approximately 20 minutes and approximately 60 minutes. An example extraction mixture is photographically depicted in FIG. 1. Demineralized bone was particulated and mixed into an aqueous medium, which was water in this example. The mixture was treated for 30 minutes with steam pressure of approximately 15 psi and temperature of approximately 120° C. to extract bone collagen from the particulate bone. The particulate bone from which the bone collagen was extracted can be seen sedimented along the bottom of the flask. The supernatant fluid contains the extracted bone collagen. The particulate bone and extracted bone collagen may be mixed by simple agitation to distribute or suspend the particulate within the liquid.

Utilization of pressure treatment as described herein may extract collagen more efficiently than conventional processes. The collagen may also be extracted partially without complete breakdown of bone as in conventional processes. In some instances, the extraction may be performed in as little as approximately 15 minutes to approximately 30 minutes. In other instances the extraction may be performed between approximately 15 minutes and approximately 45 minutes, approximately 15 minutes and approximately 60 minutes, approximately 15 minutes and approximately 60 minutes, approximately 30 minutes and approximately 45 minutes, approximately 30 minutes and approximately 60 minutes, approximately 30 minutes and approximately 90 minutes, approximately 45 minutes and approximately 60 minutes, approximately 45 minutes and approximately 90 minutes, less than approximately 45 minutes, less than approximately 60 minutes, less than approximately 90 minutes. Accordingly, the extraction process is more efficient than current methods that require application of various treatments for 12 hours or more to obtain bone collagen. Various embodiments of the present methods may be employed to minimize antigenicity of the preparation compared to current treatment processes.

Figure 2:
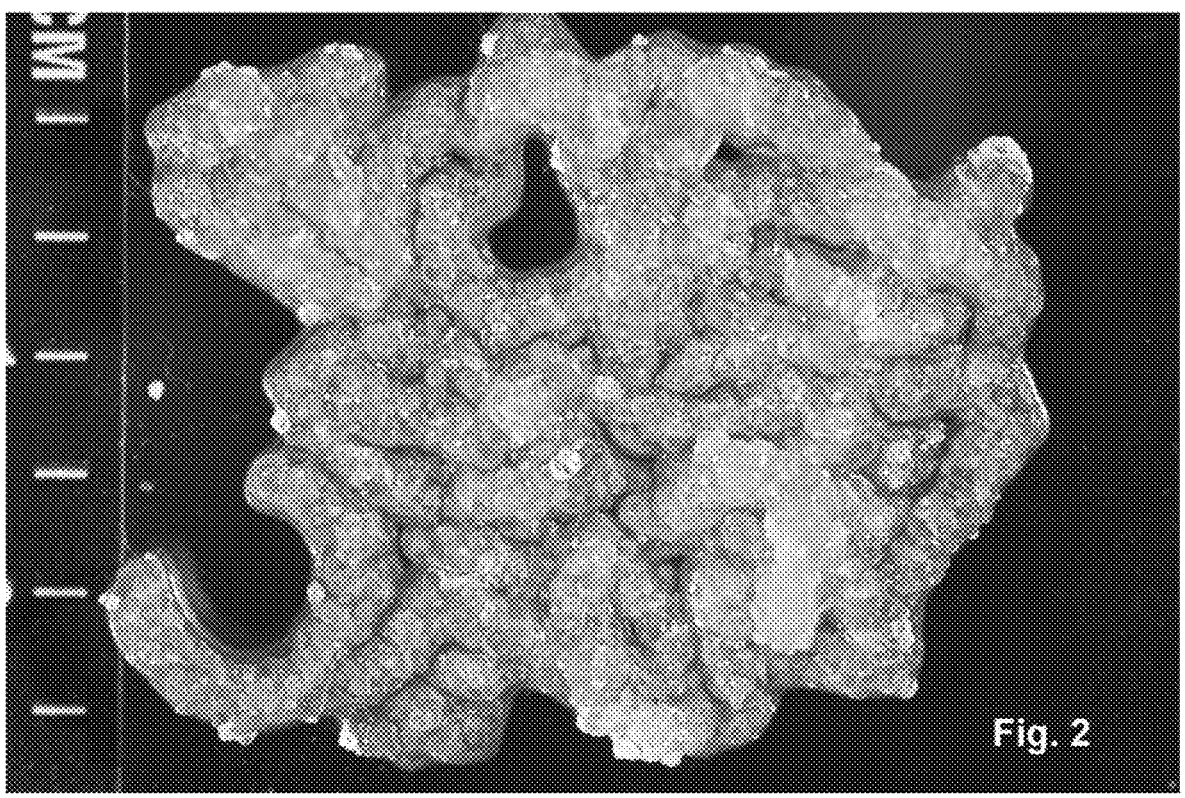
FIG. 2 is a photograph of a mixture of demineralized bone particles and bone collagen after being expressed from a syringe according to various embodiments described herein. The mixture has been prepared to have a paste consistency.

When the extraction process is complete, such as when the mixture obtains a desired thick and viscous consistency, it may be allowed to cool. As the mixture is cooled it may become gelatin-like. The mixture of bone matrix and bone particles may be contemporaneously used for surgical implantation in the treatment of bone lesions. In some embodiments, the consistency of the mixture may be modified prior to use to achieve a desired consistency, such as a gel, paste, or putty consistency. The consistency of the extraction mixture of bone matrix and bone particles may be modified by addition or removal of aqueous component. For example, the mixture may be condensed, increasing its consistency. In one embodiment, the consistency of mixture may be increased by concentrating the matrix and particles by evaporation. Additionally or alternatively, the consistency of the extraction mixture of bone matrix and bone particles may be modified by further addition of bone materials. For example, non-demineralized particles may be added to the flowable gelatinous mixture to achieve a desired consistency, such as a gel, paste, or putty consistency. Alternately or additionally, demineralized bone particles may be added to the flowable gelatinous mixture to achieve the desired consistency, such as a gel, paste, or putty consistency. The additional bone particles may have dimensions and comprises sizes similar to the bone particles from which the collagen is extracted. However, other sizes may be used. In one embodiment, the additional bone particles comprise micron scale particles. The amount of bone suspended in the preparation may be from approximately 3% to approximately 50% by weight. An example collagen-bone preparation comprising demineralized bone particles within extracted bone collagen matrix is photographically depicted in FIG. 2 (scale in cm). As shown, the preparation has been prepared to have a paste consistency and in shown after having been expressed from a conventional syringe.

Figure 3:
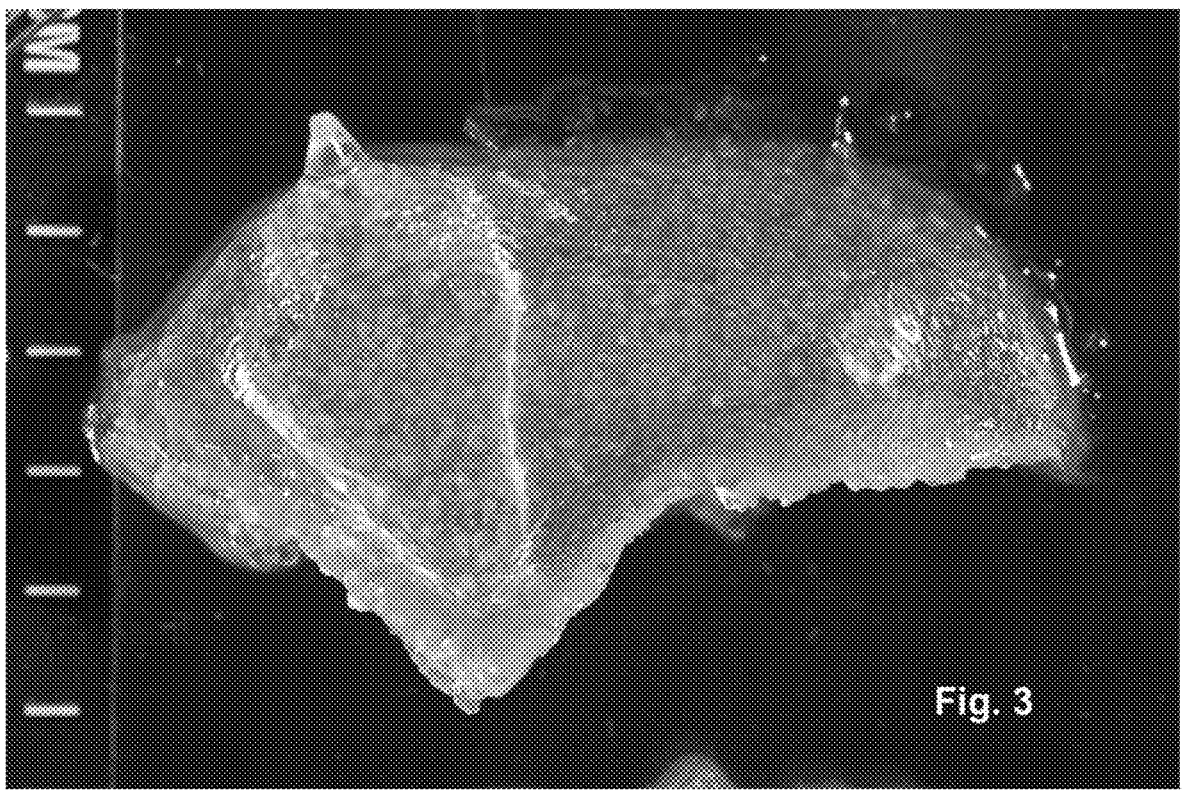
FIG. 3 is a photograph of flat freeze-dried collagen-bone particle mixture showing bone particles embedded in extracted bone collagen according to various embodiments described herein.
Figure 4:
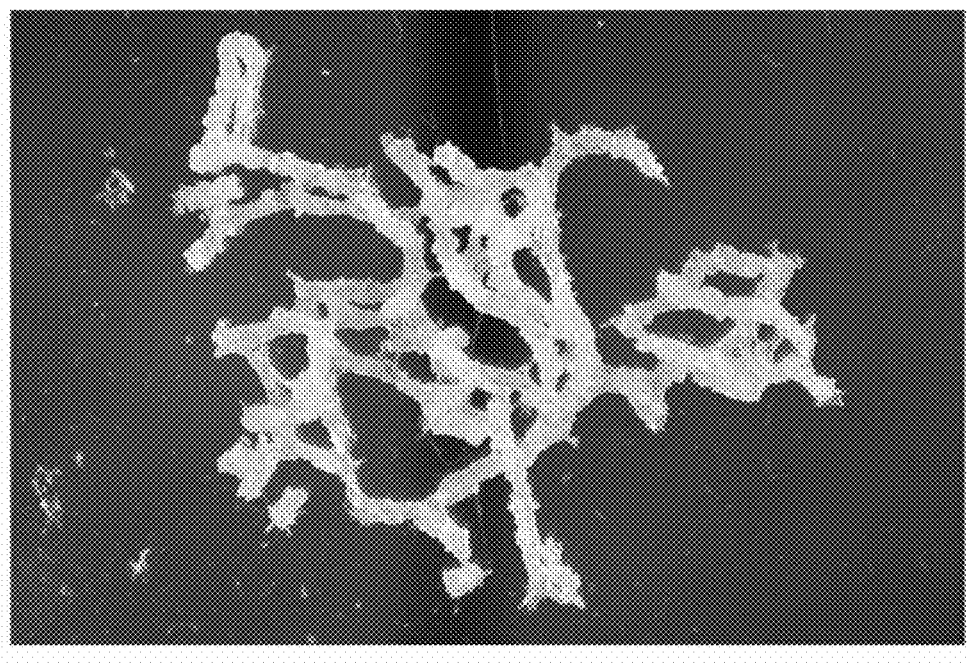
FIG. 4 is a photograph of the mixture of demineralized bone particles and bone collagen shown in FIG. 2 after being dried by freeze-drying according to various embodiments described herein.
Figure 5:
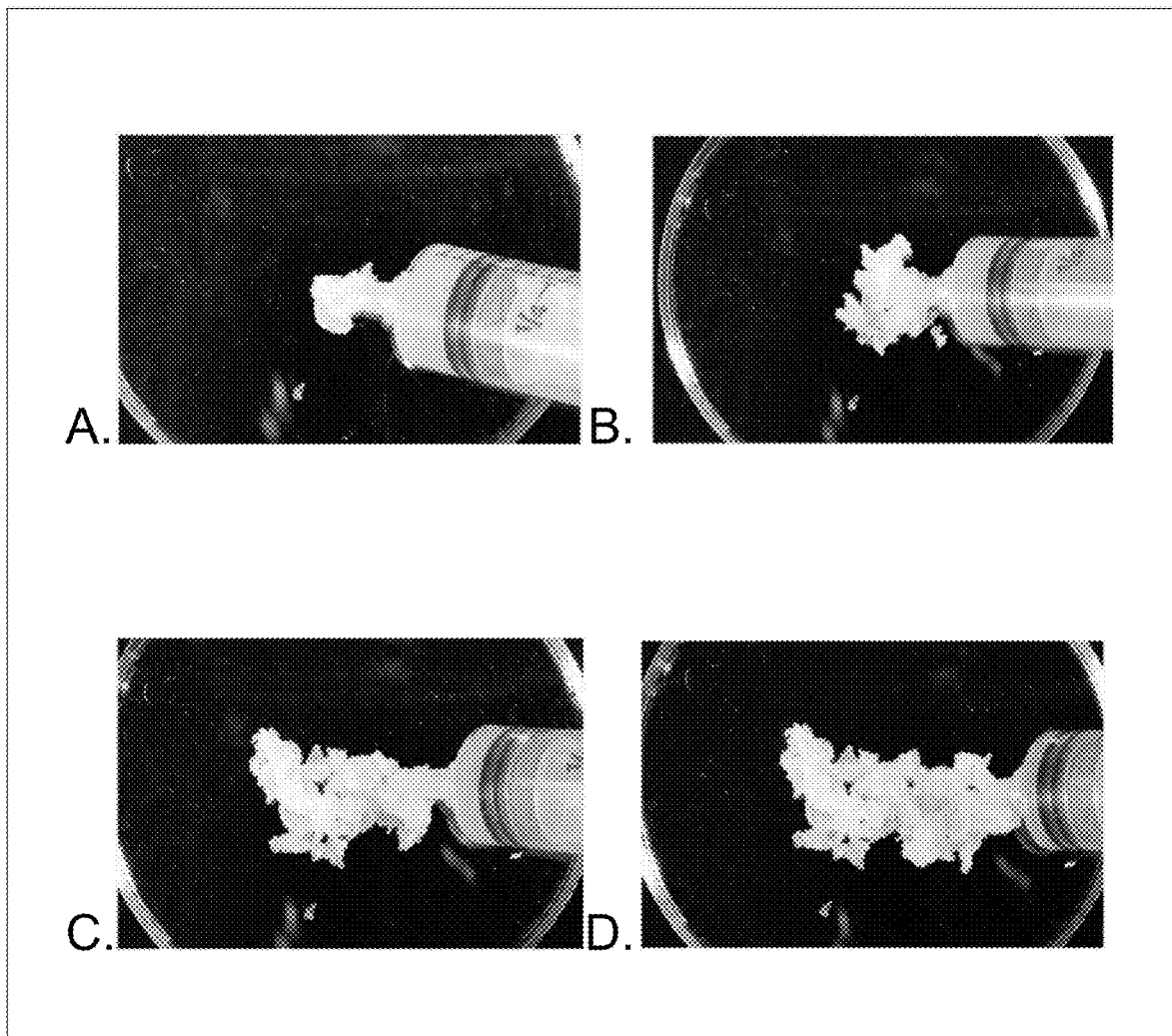
FIG. 5 is a series of photographs arranged sequentially (panels A-D) showing a reconstituted mixture of demineralized bone particles and collagen being expressed from a syringe according to various embodiments described herein.
Figure 6:
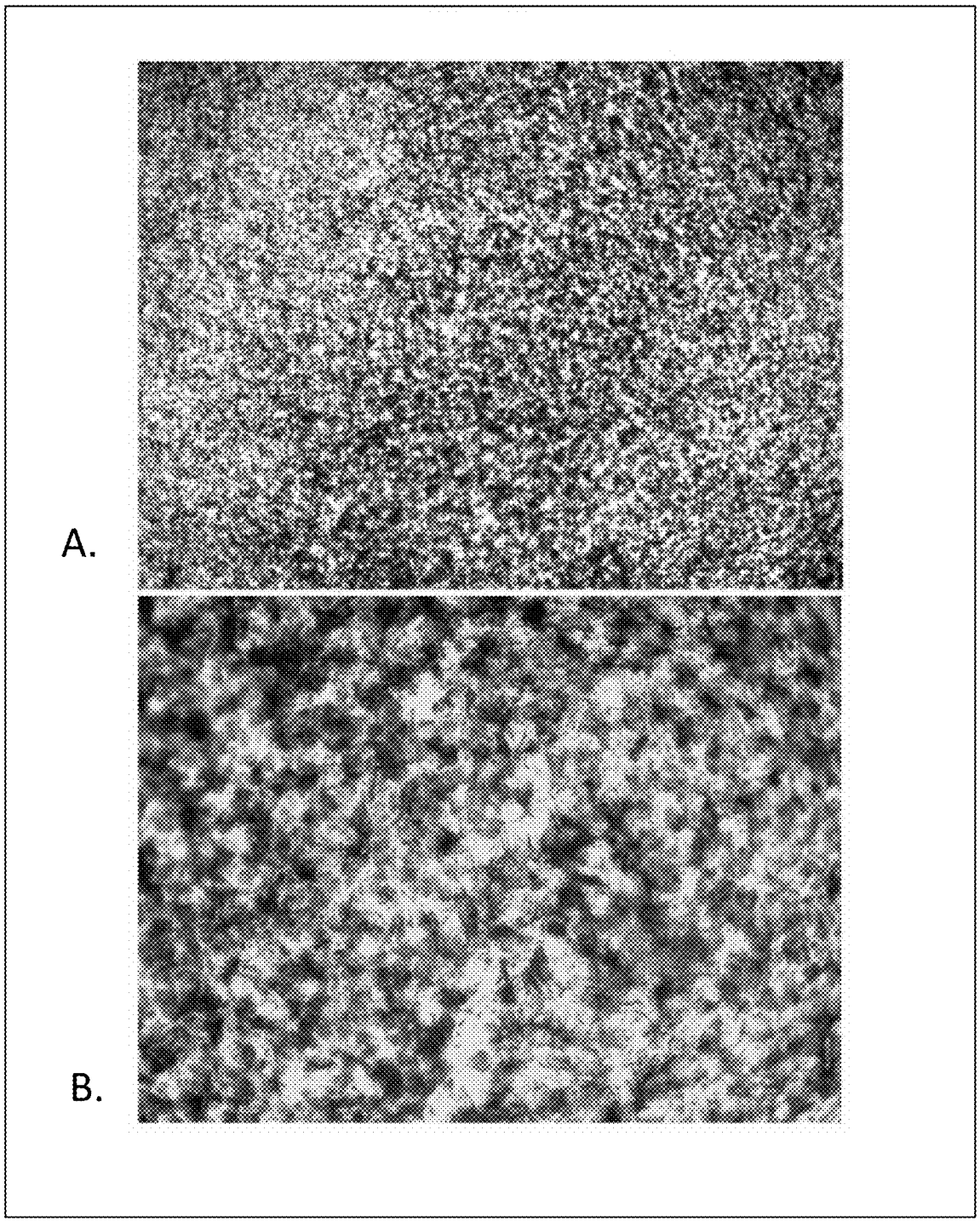
FIG. 6 provides microscopic views at ×25 magnification (panel A) and ×100 magnification (panel B) of the demineralized bone particles and collagen preparation under polarized light wherein the bone particles are clearly visible according to various embodiments described herein.

The collagen-bone preparation or extraction mixture may also be dried for storage. In various embodiments, the collagen-bone preparation or extraction is dried by freeze-drying, hypodermically dehydration, or a known method of drying to prepare the composition for storage. In one embodiment, prior to addition of bone particles to the mixture, the mixture may be preserved by drying, e.g., hypothermic dehydration, freeze-drying, chemical dehydration, or drying. An example of an extraction mixture in dry form is photographically depicted in FIG. 3 (scale in cm). The flat freeze-dried collagen-bone particle mixture comprises bone particles embedded in extracted bone collagen obtained by freeze drying the extraction mixture of FIG. 1. An example of the collagen-bone preparation comprising demineralized bone particles within extracted bone collagen of FIG. 2 after being dried by freeze-drying is photographically depicted in FIG. 4. As can be seen, when dried, the dry material may be reduced in volume. However, the volume may be restored by reconstitution with an aqueous medium such as water or salt solution, such as saline, phosphate buffered saline, lactated Ringer's solution or any given number of balanced salt solution, for example Earle's solution, Hanks solution, Guy's solution or any similar solutions. The reconstituted preparation may return to its previous form and consistency, depending on the degree of rehydration. The amount of aqueous medium used to reconstitute the preserved extraction mixture comprising the dry collagen-bone preparation may be controlled to obtain the desired consistency. For example, the preserved extraction mixture may be reconstituted with an amount aqueous medium to form a reconstituted extraction mixture having a gel, paste, or putty consistency. Reconstituting may therefore comprise controlling the amount of aqueous medium in the reconstituted extraction mixture. In one example, the concentration of collagen may be reduced by condensing the collagen in the reconstituting aqueous medium by evaporation. Additionally or alternatively, additional bone particles may be added to achieve the desired consistency. In one embodiment, the reconstituted extraction mixture may comprise between approximately 3% to approximately 50% by weight bone. Panels A-D of FIG. 5 show sequential photographic depictions of the collagen-bone preparation following reconstitution to a paste consistency, wherein the paste is easily expressed from a conventional syringe. Microscopic views of the preparation under polarized light wherein the bone particles are clearly visible are shown in at ×25 magnification (panel A) and ×100 magnification (panel B) of FIG. 6. Thus, upon reconstitution of the preserved dried collagen-bone mixture, the reconstituted mixture may assume the characteristics of the original mixture composition, e.g., the characteristics of the extraction mixture, modified extraction mixture prior to preservation, or the extraction mixture if modified to have a desired consistency, and may be used for surgical transplantation in the treatment of bone lesions.

The preparation may comprise bone particles suspended in bone collagen extracted from the same. The extraction mixture may be produced by subjecting particles of demineralized bone, partially demineralized bone, or combination thereof to a limited time exposure to high pressure and elevated temperature sufficient to extract bone collagen. The bone particles may be obtained from donor bone selected from the group consisting of allogeneic bone, xenogeneic bone, and combinations thereof. In one embodiment, the bone particles are obtained from AAA bone. In various embodiments, the bone particles are prepared in sizes between approximately 10 and approximately 900 microns. In this or another embodiment, the bone particles may be in a form of bone fluff with particles ranging from approximately 100 to approximately 3000 microns in length and approximately 40 microns to approximately 60 microns in width. Rapid extraction may be aided by employing microstranded bone particles in the form of bone fluff. In one embodiment, the extraction comprises subjecting the bone particles in solution of blood serum, water, saline, balanced salt solution, or combination thereof to pressure treatment of 15 psi or higher. In this or another embodiment, the extraction comprises subjecting the bone particles in the solution to temperature treatment at a temperature above approximately 36° C. In one embodiment, the extraction comprises contacting the bone particles with water at temperatures between approximately 60° C. and approximately 120° C. The water may comprise distilled water, saline, balanced salt solution, or combination. The choice of temperature may consider elevation. The demineralized bone-water mixture may be subjected to a pressure of at least 15 psi, 20 psi, 25 psi, 30 psi, or greater, for example. The choice of pressure may consider elevation. The pressure may be provided by steam pressure. In one embodiment, the pressure may be approximately 15 psi, greater than approximately 15 psi, or between approximately 15 psi and approximately 30 psi, and may be provided by steam. The water, or aqueous medium, and bone particles may be maintained at an average temperature of approximately 120° C. or greater than approximately 120° C. The treatment process may be carried out for approximately 15 minutes or longer, approximately 20 minutes or longer, approximately 30 minutes or longer, approximately 40 minutes or longer, approximately 50 minutes or longer, approximately 60 minutes or longer. In one embodiment, the treatment process may be carried out in approximately 60 minutes or less, approximately 50 minutes or less, approximately 40 minutes or less, approximately 30 minutes or less, approximately 20 minutes or less, or approximately 15 minutes or less.

The collagen-bone particle extraction mixture may be prepared to comprise a desired consistency, e.g., a gel, paste, or putty. In various embodiments, the collagen-bone particle extraction mixture is prepared for use by adjustment of the mixture consistency by one or more of addition or removal of aqueous component, e.g, concentrated by evaporation, or addition of additional bone particles. The consistency of the collagen-bone extraction mixture may be modified by removal of aqueous component or addition of bone particles to achieve the desired consistency. The collagen-bone particle extraction mixture or modified collagen-bone extraction mixture may be preserved by one or more of freeze-drying, hypothermic dehydration, chemical dehydration or desiccation. Aqueous medium may be added to the preserved collagen-bone particle mixture in an amount suitable to obtain a desired consistency, such as a gel, paste, or putty. The amount of bone suspended in the preparation may be from approximately 3% to approximately 50% by weight. The preparation comprising bone particles suspended in bone collagen extracted from the same, and which may further include additional demineralized or non-demineralized bone added to achieved desired consistency, may be employed for surgical transplantation in the treatment of bone lesions or other bone defects. For example, in one method of treatment, the preparation is expressed from a conventional syringe for application to the application site. The syringe may be a conventional syringe. In another embodiment, the preparation may be applied to bone lesions or defects using another delivery device such as a spatula, blade, tube, or bladder.

A kit comprising the dried bone collagen-bone particle composition is also disclosed. The kit may be provided to a user, such as a medical professional. The user may add aqueous medium to the dry collagen-bone preparation to achieve a desired consistency. The aqueous medium may be water or a salt solution, such as saline, phosphate buffered saline, lactated Ringer's solution or any given number of balanced salt solution, for example Earle's solution, Hanks solution, Guy's solution or any similar solutions. In some embodiments, the kit comprises all or a portion, such as one or more components, of the aqueous reconstitution medium. The user may also add additional bone particles, such as demineralized, partially demineralized, non-demineralized, or combinations thereof to the preparation to modify the consistency. In some embodiments, the kit may comprise the dry collagen-bone particle composition and the additional bone particles. In one embodiment, the kit comprises the dry collagen-bone particle composition, the aqueous reconstitution medium, and the additional bone particles.

A method of treating a patient may include implanting the collagen-bone composition into a bone defect of a subject to promote osteogenesis. The subject may be an animal subject, including a human subject.

In one embodiment, a demineralized bone particle mixture in the form of gel, putty or paste may be prepared in a solution of water, blood serum, saline, or any balanced salt solution at a temperature above approximately 36° C. or solution of blood serum, water, saline or any balanced salt solution at approximately 15 psi. or higher.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. In this manner, Applicant reserves the right to amend the claims during prosecution to add features as variously described in this specification, and such amendments comply with the requirements of 35 U.S.C. §§ 112(a) and 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

What is claimed is:

1. A method of making a collagen-bone mixture, the method comprising:
   contacting microparticulate bone particles with aqueous medium to form a mixture of the bone particles contacted with the aqueous medium, wherein the bone particles comprise dried demineralized bone, partially demineralized bone, or a combination thereof, wherein the bone particles have particle sizes ranging from approximately 40 microns to approximately 60 microns in width, approximately 10 microns to approximately 100 microns in thickness, and a length that is one or more orders of magnitude greater than that of the width or the thickness, wherein the length is not greater than approximately 3,000 microns; and
   extracting bone collagen from the bone particles to form an extraction mixture, wherein the extracting comprises subjecting the bone particles contacted with the aqueous medium to an elevated temperature greater than 60° C. and high pressure treatment of at least 15 psi for 50 minutes or less sufficient to extract the bone collagen from the bone particles, wherein the extraction mixture comprises the bone particles intact and the bone collagen extracted from the intact bone particles, wherein each of the intact bone particles retains a basic framework of bone.

2. The method of claim 1, wherein the pressure treatment is provided by steam, and wherein the method further comprises cooling the extraction mixture.

3. The method of claim 2, wherein the bone particles comprise bone selected from the group consisting of allogeneic bone, xenogeneic bone, and combinations thereof.

4. The method of claim 2, wherein the bone particles are from a single donor.

5. The method of claim 2, wherein the aqueous medium comprises blood serum, water, saline, balanced salt solution, or combination thereof.

6. The method of claim 2, wherein the aqueous medium contacts the bone particles at a temperature between greater than 60° C. and approximately 120° C. during the elevated temperature and high pressure treatment.

7. The method of claim 2, wherein the mixture of bone particles contacted with the aqueous medium comprises between approximately 20% to approximately 60% aqueous medium by volume, and wherein the elevated temperature and high pressure treatment is applied to achieve an extraction mixture viscosity of above approximately 2 centipoise.

8. The method of claim 2, wherein exposing the bone particles contacted with the aqueous medium to the temperature and pressure treatment-sufficient to extract the bone collagen from the bone particles comprises maintaining the bone particles contacted with the aqueous medium at an average temperature approximately 120° C. or greater.

9. The method of claim 2, wherein the bone particles contacted with the aqueous medium are partially demineralized bone particles.

10. The method of claim 2, further comprising modifying the extraction mixture to a consistency to form a modified mixture comprising a gel, paste, or putty.

11. The method of claim 10, wherein the weight ratio of collagen to bone particles in the modified mixture is between approximately 6:10 to approximately 7:10.

12. The method of claim 10, wherein modifying the consistency of the extraction mixture comprises addition of additional bone particles.

13. The method of claim 10, wherein the modified mixture comprises between approximately 3% to approximately 50% by weight bone.

14. The method of claim 10, wherein modifying the consistency of the extraction mixture comprises concentrating the collagen in the extraction mixture by evaporation.

15. The method of claim 2, further comprising preserving the extraction mixture to form a preserved extraction mixture, wherein preserving comprises drying the extraction mixture using a drying process comprising one of freeze-drying, hypothermic dehydration, chemical dehydration, or desiccation.

16. The method of claim 15, further comprising reconstituting the preserved extraction mixture with an amount of aqueous medium to form a reconstituted extraction mixture having a gel, paste, or putty consistency, wherein the aqueous medium comprises water, salt solution, or a combination thereof, and wherein the salt solution comprises saline, phosphate buffered saline, lactated Ringer's solution, balanced salt solution, or a combination thereof.

17. The method of claim 16, wherein reconstituting comprises controlling the amount of aqueous medium in the reconstituted extraction mixture.

18. The method of claim 17, wherein reconstituting further comprises addition of additional bone particles, concentration of collagen by evaporation, or a combination thereof.

19. The method of claim 16, wherein the reconstituted extraction mixture comprises between approximately 3% to approximately 50% by weight bone.

20. The method of claim 2, wherein the mixture of bone particles contacted with the aqueous medium comprises between approximately 20% to approximately 60% aqueous medium by volume.

21. The method of claim 20, wherein the pressure treatment includes steam pressure, and wherein the elevated temperature is 100° C.+/−10° C. and the high pressure is between 15 psi and approximately 30 psi.

* * * * *